United States Patent [19]

Iwasaki et al.

[11] Patent Number: 4,612,169

[45] Date of Patent: Sep. 16, 1986

[54] PROCESS FOR STERILIZATION OF ENZYME CONTAMINATED BY BACTERIA

[75] Inventors: Taisuke Iwasaki, Hachioji; Yoshihiko Honda, Sakato; Fumio Nagaoka; Sadao Aoki, both of Atsugi; Kazuo Horigome, Sagamihara; Ruyzo Imada, Ebina, all of Japan

[73] Assignee: Snow Brand Milk Products Co. Ltd., Sapporo, Japan

[21] Appl. No.: 592,010

[22] Filed: Mar. 21, 1984

[30] Foreign Application Priority Data

Mar. 25, 1983 [JP] Japan .................................. 58-50157

[51] Int. Cl.⁴ ............................................. A61L 9/00
[52] U.S. Cl. ............................. 422/32; 252/DIG. 72; 252/542; 426/64; 426/331; 435/183; 435/814; 422/28; 514/738

[58] Field of Search .................. 426/331, 64; 252/DIG. 12, 542; 422/28, 32; 424/343; 435/184, 183, 814

[56] References Cited

U.S. PATENT DOCUMENTS

| | | | |
|---|---|---|---|
| 4,140,802 | 2/1979 | Kelly et al. | 426/331 |
| 4,142,999 | 3/1979 | Bloching et al. | 252/117 |
| 4,298,624 | 11/1981 | Mehring et al. | 426/532 |
| 4,356,267 | 10/1982 | Callegaro et al. | 210/927 |

Primary Examiner—Barry S. Richman
Assistant Examiner—Titus Ledbetter, Jr.
Attorney, Agent, or Firm—Cushman, Darby & Cushman

[57] ABSTRACT

An enzyme contaminated by bacteria during preservation or repeated use thereof is sterilized by immersing the enzyme contaminated mass in a polyvalent alcohol. This procedure does not inactivate the enzyme.

2 Claims, 2 Drawing Figures

PROCESS FOR STERILIZATION OF ENZYME CONTAMINATED BY BACTERIA

BACKGROUND OF THE INVENTION (a) Field of the Invention

The present invention relates to a process for sterilization of an enzyme contaminated by bacteria during preservation or repeated use of the enzyme.

(b) Description of the Prior Art

There are many cases where an enzyme is contaminated by bacteria during preservation of the enzyme or repeated use of the enzyme. For instance, during the use of an enzyme dissolved in an aqueous solution, bacteria contaminate the solution, and during the repeated use of a so-called immobilized enzyme, bacteria adhere to the immobilized enzyme to cause the reduction of the enzymatic actitivy.

Particularly, in the case of the immobilized enzyme wherein the substrate of the enzyme has a composition of components favorable to the growth of bacteria, and in the case where the treatment conditions in the use of a immobilized enzyme are environmentally favorable to the growth of the bacteria, the contamination of the enzyme by bacteria becomes significant.

In addition, in the immobilized enzyme which has been contaminated by bacteria, not only the reduction of the enzymatic activity but also the deterioration of the quality of the substrate to which the enzyme has been applied becomes noticeable.

For instance, at present, lactose hydrolyzed whey syrups and lactose hydrolyzed milk are industrially produced by using an immobilized lactase. The immobilized lactase is prepared by bringing lactase, which hydrolyzes lactose in animal's milk into glucose and galactose, into chemical bonding with a water-insoluble carrier, for instance, chitin and resin or by entrapping lactase in cellulose triacetate, polyacrylamide gel, etc.

However, in the utilization of such an immobilized lactase, the immobilized lactase is generally used continuously and repeatedly in the conditions packed within a reactor. Namely, the mode of utilization of the immobilized lactase is different from the batch-wise use of free lactase. Accordingly, in the treatment of the milk even if the sterilized milk is used and the reactor and the mechanical apparatus to which the sterilized milk is brought into contact are to be treated by sterilization, proliferation of microorganisms during the repeated use of the immobilized enzyme packed in the reactor is unavoidable, and as a result of increased number of contaminating bacteria, the quality of the above-mentioned products become deteriorated. Consequently, it becomes unavoidable to limit the number of times of repeated use of the immobilized lactase resulting in disadvantage in cost.

In consideration of the above-mentioned situations, several treatments have been devised in the case of utilization of an enzyme or an immobilized enzyme and, for instance, the raw material is treated under conditions as aseptic as possible or under conditions which are unsuitable for the proliferation of the microorganisms, for instance, at a low temperature below 10° C. or at a high temperature of 60° to 70° C.

However, there are problems of operation and production cost in keeping the enzymatic reaction system under aseptic conditions, and in addition, the enzymatic reaction is not effective and practical in a low temperature range. On the other hand, in a high temperature range, the reduction of enzymatic activity is unavoidable except for specified enzymes such as heat-resistant enzymes, for instance, glucose-isomerase, and the immobilized enzyme thereof.

In addition, as a means of carrying out sterilization of the contaminated enzyme by bacteria or of the substrate system on which the contaminated enzyme reacts or carrying out the removal of bacteria therefrom without reducing the enzymatic activity or inactivating the enzyme, sterilization by a bactericidal agent or removal of bacteria by a membrane filter is considered, however, the application of the bactericidal agent is limited in the utilization of enzymes in the field of foodstuffs, and there is the disadvantage that the removal of bacteria by a membrane filter is difficult to be applied to the substrate system, for instance, milk protein containing colloidal substances except for those substrate systems of a simple composition comprising low-molecular components.

As has been stated above, a practical process for effectively sterilizing the contaminated enzyme by bacteria has not been found.

The present inventors have found that by immersing the enzyme contaminated with bacteria into a polyvalent alcohol, the enzyme can be sterilized effectively without substantially causing the reduction of enzymatic activity thereof or the inactivation thereof, and have attained the present invention.

SUMMARY OF THE INVENTION

The main object of the present invention is to provide a process for effectively sterilizing an enzyme contaminated by bacteria without substantially causing the reduction of enzymatic activity thereof or the inactivation thereof. The other object of the present invention will be made clear from the following description:

The characteristic feature of the present invention lies in a treatment of immersing the enzyme contaminated by bacteria into a polyvalent alcohol, thereby sterilizing the enzyme.

DETAILED DESCRIPTION OF THE INVENTION

The enzyme treated in the present invention as the subject is an enzyme in a liquid state, an enzyme in a powdery state or an immobilized enzyme and includes those contaminated by bacteria due to their use, their preservation or the like.

The "polyvalent alcohol" used in the present invention for sterilizing the enzyme contaminated by bacteria have 2 to 3 hydroxyl groups within the molecule thereof, and includes glycerol, ethylene glycol, propylene glycol, 1,3-butanediol, 1,4-butanediol, 2,3- butanediol, 1,5-pentanediol, 1,6-hexanediol, 1,2-butanediol, 1,2,4-butanetriol, 1,2,6-hexanetriol and the like.

According to the process of the present invention, the enzyme contaminated by bacteria is immersed into one of the above-mentioned polyvalent alcohols or a mixture of at least two thereof, and it is preferable to immerse the contaminated enzyme into an aqueous solution of a content of more than 30% by weight of one polyvalent alcohol or an aqueous solution of a content of more than 30% by weight of the mixture of at least two thereof. The immersion is preferably carried out for 3 hours to 5 days at a temperature of usually 20° to 40° C.

In case of immersion, since the sterilization effect is reduced at a temperature below 20° C., and on the other hand, the enzymatic activity is affected at a temperature over 40° C., it is necessary to pay attention to the immersion temperature, however, in the case of sterilizing a thermo-stable enzyme, a higher temperature of immersion may be used.

In addition, even in the above-mentioned temperature range, when the higher temperature is applied a higher sterilization effect is obtained after the shorter time of immersion, for instance, a few hours. And, at the same temperature, the higher the concentration of the polyvalent alcohol and the longer the immersion time, the more improved sterilization effect is available.

Figure 1:
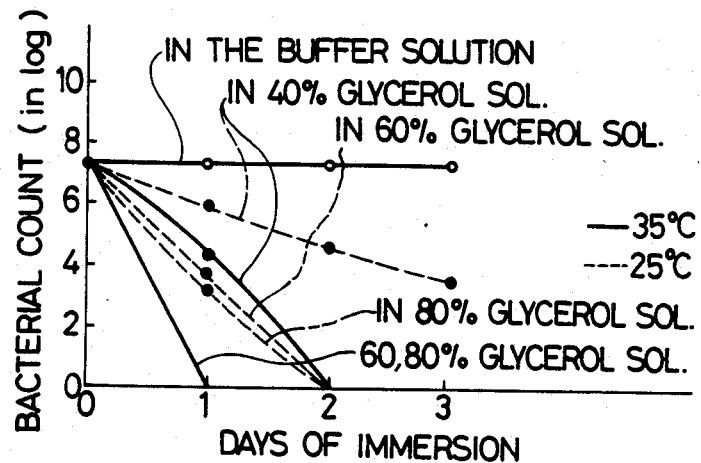
FIG. 1 shows, in the case where a mass of an enzyme contaminated by bacteria is immersed into an aqueous solution of glycerol, the effects of the concentration of glycerol therein, the temperature and the time of immersion, respectively on the reduction of the number of bacteria on/in the contaminated enzyme.

FIG. 1 shows the test results on the relationship between the number of bacteria and the concentration of glycerol, the temperature and the time of immersion in the case where the immobilized lactase was used as the subject and immersed into an aqueous solution of glycerol. Namely, in the test, a growth culture of the bacteria contaminating the immobilized enzyme was added to each of the aqueous solutions of glycerol at several concentrations of $1.8 \times 10^7$ cells/ml of the solution, and the change in bacterial number was observed while keeping the solution at 35° C. and 25° C., respectively, the number of bacteria being determined by the membrane-filter method. As a control, those inocula in a phosphate buffer solution instead of the aqueous glycerol solution were used.

As is clearly seen in FIG. 1, even in the cases where the concentration of glycerol was constant, the reduction of bacterial number appeared sooner in the inoculum at the higher temperature of immersion, and on the other hand, even in the cases where the temperature was constant, a remarkable reduction of bacterial number was seen in a shorter time of immersion at a higher concentration of glycerol. On the other hand, substantial reduction of the bacterial number was not observed in the buffer solution.

Figure 2:
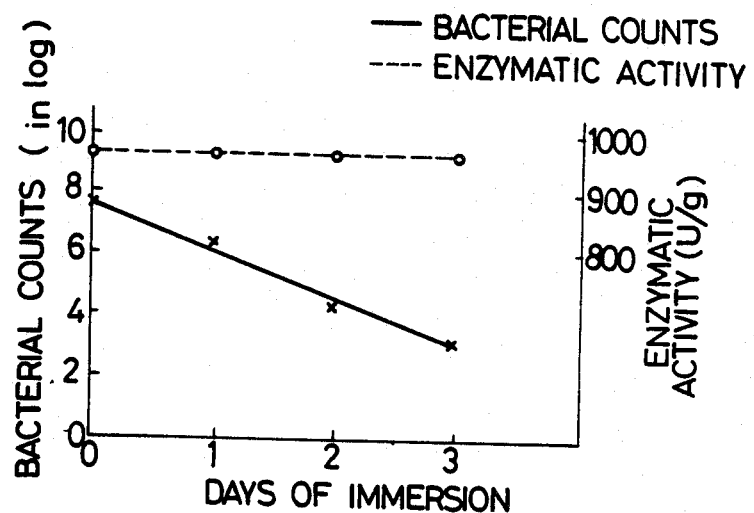
FIG. 2 shows, in the case where the immobilized lactase contaminated by bacteria is immersed into an aqueous solution of glycerol, the effects of the time of immersion on the number of bacteria on/in the immobilized lactase and the enzymatic activity of the immobilized lactase.

FIG. 2 shows the test results concerning the effect of time of immersion on the bacterial number and the enzymatic activity in the case where the immobilized lactase contaminated by bacteria (at $3.0 \times 10^7$ cells/g of the immobilized lactase) was immersed in an aqueous 60% by weight solution of glycerol for 1 to 3 days while using an inoculum in a buffer solution as a control.

As seen in FIG. 2, the time-dependent reduction of the bacterial number was observed in the aqueous solution of glycerol, and on the other hand, such a substantially time-dependent reduction was not observed on the enzymatic activity.

Namely, it is understandable that even the heavily bacteria contaminated immobilized enzyme can be effectively sterilized without impairing the enzymatic activity thereof according to the process of the present invention by immersing the contaminated immobilized enzyme into the above-specified polyvalent alcohol.

It is considered that the above-mentioned sterilizing effect of the polyvalent alcohol is not clear but may be responsible for the high osmotic action of the polyvalent alcohol on the bacterial cells. In this connection, as a substance known to exhibit such as osmotic action on the bacterial cells, for instance, dimethylsulfoxide (DMSO), glucose, sucrose, sorbitol and the like may be mentioned, and among them, there are some which exhibit the sterilizing effect such as DMSO, however, DMSO has the disadvantages of giving unfavorable effects on the enzymatic activity and giving an offensive smell to the enzyme itself, and in glucose, sucrose and sorbitol, only a low sterilizing effect is recognized.

In this connection, Table 1 shows the test results of immersing the immobilized lactase contaminated by bacteria into the respective aqueous solutions of the polyvalent alcohols by the present invention and the above-mentioned substances. The test was carried out as follows:

TEST METHOD

Immobilized lactase contaminated by bacteria was immersed into each of the aqueous solutions of the respective substances shown in Table 1 at $1.3 \times 10^8$ cells/ml of the solution for 1 to 2 days, and the time-dependent effects of the substance on the reduction of the bacterial number and on the enzymatic activity were determined. In addition, the concentration of propylene glycol, ethylene glycol and DMSO was adjusted to exhibit the osmotic pressure of the solution thereof corresponding to that of the aqueous 60% by weight solution of glycerol, namely, 6780 mOsm/l.

Since it was difficult to adjust the concentration of sorbitol and glucose to exhibit the osmotic pressure corresponding to that of the aqueous 60% by weight solution of glycerol, the concentration of sorbitol or glucose was 70% and 50% by weight, respectively.

TABLE 1

| Substance | Concentration (% by weight) | Osmotic pressure of 100% by weight | Number of bacteria (per ml) after | | Effect on enzymatic activity |
|---|---|---|---|---|---|
| | | | one day | Two days | |
| Glycerol | 60 | 11300 | $3 \times 10^6$ | 29,000 | — |
| Propylene glycol | 52.3 | 12900 | 1,000 | <100 | — |
| Ethylene glycol | 40 | 16800 | 8,900 | <100 | — |
| Sorbitol | 70 | 6000 | $3.8 \times 10^8$ | $1.2 \times 10^8$ | + |
| Glucose | 50 | 6200 | $3.5 \times 10^8$ | $5.2 \times 10^7$ | + |
| DMSO | 49.3 | 13600 | 1,000 | <100 | + |

Notes: — denotes no effect and + denotes adverse effects (lowers enzymatic activity).

As seen in Table 1, sorbitol and glucose not only did not exhibit any substantial sterilization effect on the immobilized lactase contaminated by bacteria but also affected the activity of the lactase itself, and on the other hand, a remarkable sterilization effect was found on the immobilized lactase immersed in the polyvalent alcohol according to the present invention without any effect on the activity of lactase. In this connection, the fact that lactases are easily inactivated was used in the present test although the stability of the lactases depends on the origin from which the lactases are derived, the superiority of the process for sterilizing the enzyme according to the present invention is understandable.

The process for sterilizing an enzyme contaminated by bacteria according to the present invention has been explained above by using lactase as an example of the enzyme, and since the same sterilizing effect is recognizable on the other enzyme, it can be said that the present invention contributes largely to the enzyme-utilizing industries in general.

The present invention will be explained more concretely while referring to the non-limitative examples as follows:

EXAMPLE 1

In 100 ml of an aqueous 60% by weight solution of glycerol (food additive grade), 10 g of a powdery lactase which had been heavily contaminated by bacteria at $1.2 \times 10^6$ bacterial cells/g of the powdery lactase were immersed, and after leaving the immersion for 3 days at 25° C., the viable bacterial counts were determined to be less than 100/g of the immersion liquid. The activity of the lactase at the time of immersion was 4150 U/ml of the immersion liquid, and the activity of the lactase after 3 days of immersion was 4120 U/ml of the immersion liquid.

By adding 20 g of the glycerol solution in which the contaminated lactase had been thus immersed, into 10 liters of preliminarily sterilized skimmed milk during reaction at 10° C. for 18 hours, 80% of lactose hydrolyzed milk was obtained.

EXAMPLE 2

Into a column of 7 cm in diameter and 35 cm in length, 1 liter of the immbolized lactase entrapped in cellulose triacetate was packed, and a 10% skimmed milk was continuously passed therethrough in an upflow at a reaction temperature of 7° C. and a space velocity (S.V.) of 1. Proliferation of bacteria was begun as the time passed by, and an adhesion of milk protein and an accumulation of contaminating bacteria onto the immobilized lactase were observed. At the time when the adhered amount of milk protein became 17 micrograms per mg of the immobilized lactase and the number of bacteria became $1.4 \times 10^6$/g of the immobilized lactase, the immobilized lactase was transferred from the column to the washing tank, and after washing thereof with a phosphate buffer solution of pH of 7.0, thereby sufficiently removing the milk solid therefrom, and the moisture of immobilized lactase was removed, the immobilized lactase was transferred to a preliminary sterilized vessel of 10 liters in capacity. After adding 10 liters of an aqueous 60% by weight solution of glycerol which had been sterilized for 10 min at 85° C. and cooled to 25° C. into the vessel and gently stirring the mixture, the mixture was left at 25° C. for 2 days under tight closure for prevention of contamination by bacteria.

In the above-mentioned operation, the number of bacteria adhered onto the immobilized lactase was reduced to $2 \times 10^2$/g of the immobilized lactase. After collecting the thus treated immobilized lactase from the solution of glycerol, washing thereof with a phosphate buffer solution and removing the moisture of immobilized lactase, thereby removing glycerol therefrom, the thus treated immobilized lactase was again packed into the column, and the passage of the skimmed milk therethrough was commenced. The catalytic activity of the thus sterilized immobilized lactase was 950 U/g, the enzymatic activity being almost the same as that before sterilization by glycerol, 960 U/g of the immobilized lactase.

EXAMPLE 3

Five liters of an immobilized lactase bound to a resin by covalent bonds was packed into a column of 12 cm in diameter and 60 cm in length, and 10% of skimmed milk was continuously passed through the column in down flow at a reaction temperature of 40° C. and a space velocity (S.V.) of 10. The number of bacteria in the immobilized lactase increased with the time of treatment.

At the time when the number of bacteria attained to $3.8 \times 10^6$ per gram of the immobilized lactase, the passage of the solution of skimmed milk was stopped, and after washing the column well with milipore-filtered water to remove the solid component of the milk as far as possible, the immobilized lactase was removed from the column, dehydrated and placed in a preliminarily sterilized vessel of 60 liters in capacity. Fifty liters of an aqueous 80% by weight solution of propylene glycol sterilized for 10 min at 85° C. and cooled to 35° C. was added to the immobilized lactase, and the mixture was gently stirred.

Then the immobilized lactase was tightly closed in the vessel for preventing contamination of bacteria, and left for one day in a room kept at 35° C. By the above-mentioned operation, the number of bacteria adhered to the immobilized lactase was reduced to $4.0 \times 10^2$ per gram of the immobilized lactase.

After collecting the thus treated immobilized lactase as aseptic as possible from propylene glycol solution, it was packed in the same column and after passing filtered water through the column to remove the remaining propylene glycol, the passage of the skimmed milk was resumed. The activity of the thus treated immobilized lactase was 1200 U/g showing almost no change from the activity before sterilization of 1230 U/G of the immobilized lactase.

What is claimed is:

1. A process of sterilizing an immobilized enzyme mass contaminated by bacteria, comprising the step of immersing said enzyme mass into a composition consisting of an aqueous solution of at least one polyvalent alcohol having 2 to 3 hydroxyl groups, from the group consisting of glycerol, propylene glycol and ethylene glycol in a concentration of 40–60% by weight for a period of from 3 hours to 5 days.

2. A process according to claim 1, wherein said immersion is carried out at a temperature of 20° to 40° C.

* * * * *